US012807487B2

(12) United States Patent
Mortensen et al.

(10) Patent No.: US 12,807,487 B2
(45) Date of Patent: Nov. 24, 2026

(54) HYDROCARBON UPGRADING TO METHANOL AND HYDROGEN PRODUCT STREAMS

(71) Applicant: TOPSOE A/S, Kgs. Lyngby (DK)

(72) Inventors: Peter Mølgaard Mortensen, Roskilde (DK); Charlotte Stub Nielsen, Holte (DK)

(73) Assignee: TOPSOE A/S, Kgs. Lyngby (DK)

( * ) Notice: Subject to any disclaimer, the term of this patent is extended or adjusted under 35 U.S.C. 154(b) by 631 days.

(21) Appl. No.: 18/256,335

(22) PCT Filed: Dec. 14, 2021

(86) PCT No.: PCT/EP2021/085611
§ 371 (c)(1),
(2) Date: Jun. 7, 2023

(87) PCT Pub. No.: WO2022/128993
PCT Pub. Date: Jun. 23, 2022

(65) Prior Publication Data

US 2024/0140791 A1 May 2, 2024

(30) Foreign Application Priority Data

Dec. 15, 2020 (EP) .................................... 20214171

(51) Int. Cl.
*C01B 3/26* (2006.01)
*C07C 31/04* (2006.01)

(52) U.S. Cl.
CPC ................ *C01B 3/26* (2013.01); *C07C 31/04* (2013.01); *C01B 2203/0244* (2013.01);
(Continued)

(58) Field of Classification Search
None
See application file for complete search history.

(56) References Cited

U.S. PATENT DOCUMENTS 6,100,303 A * 8/2000 Hirotani .................. C01B 3/382
518/703
9,969,666 B1 5/2018 Roesch et al.
(Continued)

FOREIGN PATENT DOCUMENTS

EP 1860088 A1 11/2007
EP 2023067 A1 * 2/2009 ............... C01B 3/16
(Continued)

OTHER PUBLICATIONS

Notification of Reasons for Refusal issued by the Japan Patent Office for Japanese Patent Application No. 2023-534350 dated Nov. 12, 2025 with English translation, 8 pages.
(Continued)

*Primary Examiner* — Anthony J Zimmer
*Assistant Examiner* — Zachary John Baum
(74) *Attorney, Agent, or Firm* — Boone IP Law

(57) ABSTRACT

The invention relates to a method and a system for upgrading a hydrocarbon-containing feed gas to a methanol product stream and a hydrogen product stream. As part of the method/system, a synthesis gas stream is compressed to a pressure being higher than the feed pressure of the hydrocarbon feed gas, prior to being fed to a methanol synthesis unit. A hydrogen product stream is provided by separating a hydro-gen rich stream, downstream the methanol synthesis unit.

15 Claims, 5 Drawing Sheets

(52) U.S. Cl.
CPC ................ *C01B 2203/0283* (2013.01); *C01B 2203/061* (2013.01); *C01B 2203/1235* (2013.01); *C01B 2203/148* (2013.01); *C01B 2203/168* (2013.01); *C01B 2203/169* (2013.01); *C01B 2203/86* (2013.01)

(56) References Cited

U.S. PATENT DOCUMENTS

| | | | |
|---|---|---|---|
| 2002/0085963 | A1 | 7/2002 | Vidalin |
| 2018/0258019 | A1 | 9/2018 | Roesch |

FOREIGN PATENT DOCUMENTS

| | | | |
|---|---|---|---|
| JP | 2004315473 | A | 11/2004 |
| JP | 2007217391 | A | 8/2007 |

OTHER PUBLICATIONS

Communication dated Jun. 1, 2021 and European Search Report dated May 21, 2021 issued by the European Patent Office in corresponding European Application No. 20214171.9-1108. (7 pages).

International Search Report (PCT/ISA/210) and Written Opinion (PCT/ISA/237) mailed on Mar. 14, 2022 by the European Patent Office as the International Searching Authority for International Application No. PCT/EP2021/085611. (12 pages).

* cited by examiner

HYDROCARBON UPGRADING TO METHANOL AND HYDROGEN PRODUCT STREAMS

FIELD OF THE INVENTION

The invention relates to a method and a system for upgrading a hydrocarbon-containing feed gas to a methanol product stream and a hydrogen product stream.

BACKGROUND

Globally, the preferred route for hydrogen production is by steam methane reforming. However, with the increasing focus on climate change, focus on the $CO_2$ emissions associated with extracting hydrogen from $CH_4$ are increasing. It is therefore becoming increasingly attractive to look at production of hydrogen with associated $CO_2$ capture, via the so-called "blue hydrogen" route.

Typically, this route involves an amine wash $CO_2$ separation process on the synthesis gas produced, which selectively extracts the $CO_2$ from the pressurized synthesis gas. However, this occurs at the expense of providing a low-pressure $CO_2$ product. Such a low-pressure $CO_2$ product typically needs subsequent compression for integration into other uses/applications. Demand for $CO_2$ is also low, and the best use of low-pressure $CO_2$ is often sequestration in a natural gas reservoir, with associated technical difficulties and cost.

It is an object of the invention to address the problems associated with the prior art, in particular to obtain complete or substantially complete utilization of the carbon from blue hydrogen production.

SUMMARY OF THE INVENTION

The present invention describes a method for upgrading a hydrocarbon-containing feed gas to a methanol product stream and a hydrogen product stream, comprising the steps of:

- a) providing a hydrocarbon-containing feed gas to a reforming reactor,
- b) reforming said hydrocarbon-containing feed gas in the reforming reactor, to provide a first synthesis gas stream,
- b1) optionally, feeding at least part of the first synthesis gas stream from step b) to a water gas shift reactor to provide shifted synthesis gas stream,
- c) cooling said first synthesis gas stream and/or the shifted synthesis gas stream in a cooling unit, to provide a second synthesis gas stream,
- d) removing water from said second synthesis gas stream, in a water removal unit, to provide a third synthesis gas stream,
- e) compressing said third synthesis gas stream in a compressing unit to a first pressure, said first pressure being higher than the feed pressure of said hydrocarbon feed gas, to provide a fourth synthesis gas stream,
- e1) optionally, feeding at least part of the fourth synthesis gas stream from step e) to a $CO_2$ removal unit, to provide a $CO_2$-rich stream and a fifth synthesis gas stream,
- f) feeding at least part of the fourth synthesis gas stream and/or at least part of the fifth synthesis gas stream from step (e) to a methanol synthesis unit, to provide a methanol-rich stream,
- g) feeding at least part of the methanol-rich stream from step f) to a separation unit, to provide a methanol product stream and a hydrogen rich stream.

A system for upgrading a hydrocarbon-containing feed gas to a methanol product stream and a hydrogen product stream is also provided, said system comprising:

- a hydrocarbon-containing feed gas arranged to be fed to a reforming reactor,
- a reforming reactor arranged to reform said hydrocarbon-containing feed gas; to thereby provide a first synthesis gas stream from the reforming reactor,
- optionally, a water gas shift reactor arranged to receive at least part of the first synthesis gas stream from the reforming reactor and provide shifted synthesis gas stream,
- a cooling unit arranged to cool said first synthesis gas stream and/or the shifted synthesis gas stream and thereby provide a second synthesis gas stream,
- a water removal unit arranged to remove water from said second synthesis gas stream, and thereby provide a third synthesis gas stream,
- a compressing unit arranged to compress said third synthesis gas stream to a first pressure, said first pressure being higher than the feed pressure of said hydrocarbon feed gas, and thereby provide a fourth synthesis gas stream,
- optionally, a $CO_2$ removal unit, arranged to receive at least a part of the fourth synthesis gas stream and to provide a $CO_2$-rich stream and a fifth synthesis gas stream,
- a methanol synthesis unit arranged to convert at least part of the fourth synthesis gas stream and/or at least part of the fifth synthesis gas stream to a methanol-rich stream,
- a separation unit, arranged to provide a methanol product stream and a hydrogen rich stream from at least part of the methanol-rich stream.

The present invention thus provides an alternative method/system for blue hydrogen production, where a combination of a cryogenic $CO_2$ separation unit and a methanol reactor is used to optimise carbon extraction from the synthesis gas. These two units (cryogenic $CO_2$ separation unit and a methanol reactor) are preferentially operated at elevated, and similar, pressures, and therefore work well as sequential operations. In this way the $CO_2$ product is valorized, and also made much easier to handle as either high pressure $CO_2$ or liquid raw methanol.

A synergy between the $CO_2$ separation and the methanol reactor can also be utilized, because the combination allows the method/system of the invention to switch between a high $CO_2$ production, with low MeOH production, and high $H_2$ production. Alternatively, production can be switched to a low $CO_2$ production, high MeOH production, and lower $H_2$ production.

DETAILED DESCRIPTION

Figure 1:
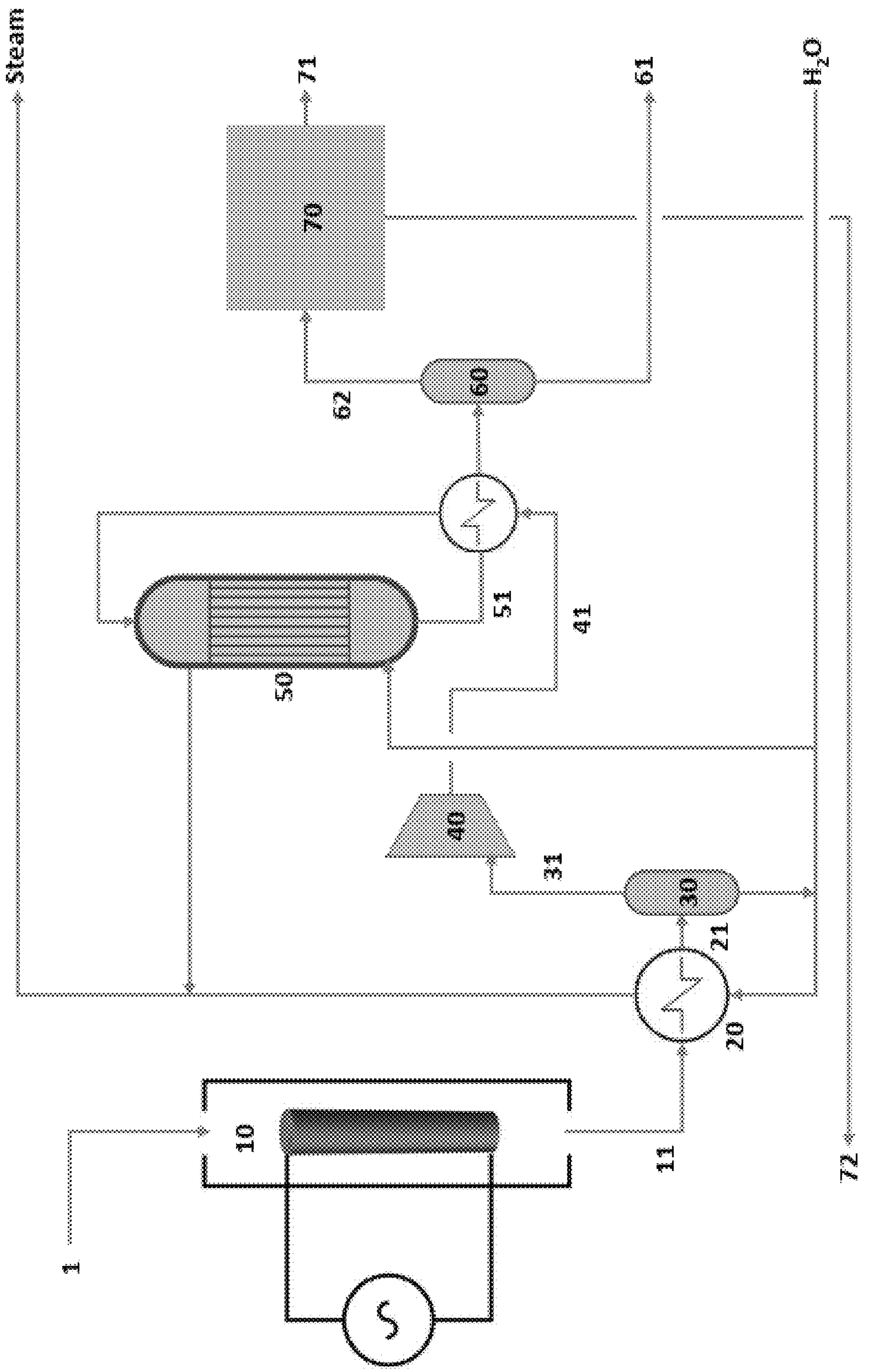
FIG. 1 is a schematic drawing of a system for upgrading a hydrocarbon feed gas to a methanol product stream and a hydrogen product stream.

Unless otherwise specified, any given percentages for gas content are % by volume. The module M of a synthesis gas is defined as $$M = \frac{H_2 - CO_2}{CO + CO_2}.$$

In a first aspect, a method for upgrading a hydrocarbon-containing feed gas to a methanol product stream and a hydrogen product stream is provided.

In the first step (a) of the method, a hydrocarbon-containing feed gas is provided to a reforming reactor. In this context, the term "hydrocarbon-containing feed" is meant to denote a gas with one or more hydrocarbons and possibly other constituents. Thus, a hydrocarbon-containing feed typically comprises a hydrocarbon gas, such as $CH_4$ and optionally also higher hydrocarbons often in relatively small amounts, in addition to small amounts of other gasses. Higher hydrocarbons are components with two or more carbon atoms such as ethane and propane. Examples of "hydrocarbon-containing feed" may be natural gas, town gas, naphtha or a mixture of methane and higher hydrocarbons, biogas or LPG. Hydrocarbons may also be components with other atoms than carbon and hydrogen such as oxygen or sulfur.

The hydrocarbon-containing feed may additionally comprise—or be mixed with one more co-reactant feeds—steam, hydrogen and possibly other constituents, such as carbon monoxide, carbon dioxide, nitrogen and argon. Typically, the hydrocarbon-containing feed has a predetermined ratio of hydrocarbon, steam and hydrogen, and potentially also carbon dioxide. The hydrocarbon feed will—in most practical applications—contain steam.

In one aspect, the hydrocarbon-containing feed is a biogas. Biogas is a mixture of gases produced by the breakdown of organic matter in the absence of oxygen. Biogas can be produced from raw materials such as agricultural waste, manure, municipal waste, plant material, sewage, green waste or food waste. Biogas is primarily methane ($CH_4$) and carbon dioxide ($CO_2$) and may have small amounts of hydrogen sulfide ($H_2S$), moisture, siloxanes, and possibly other components. Up to 30% or even 50% of the biogas may be carbon dioxide.

The hydrocarbon-containing feed may have gone through at least steam addition (present as a co-reactant feed) and optionally also pretreatment (described in more detail in the following).

In an embodiment, the hydrocarbon-containing feed is a mixture of $CH_4$, CO, $CO_2$, $H_2$, and, $H_2O$, where the concentration of $CH_4$ is 5-50 mole %, the concentration of CO is 0.01-5%, the concentration of $CO_2$ is 0.1 to 50%, the concentration of $H_2$ is 1-10%, and the concentration of $H_2O$ is 30-70%.

The term "hydrocarbon-containing feed gas" is meant to cover both the hydrocarbon-containing feed gas as well as a purified hydrocarbon-containing feed gas and a hydrocarbon-containing feed gas with added steam and/or with added hydrogen and/or with added off-gas from the methanol synthesis unit. All constituents of the hydrocarbon-containing feed gas are pressurized, either separately or jointly, upstream the reforming reactor. The pressure(s) of the constituents of the hydrocarbon-containing feed gas is/are chosen so that the pressure within the reforming reactor lies between 5 to 50 bar, preferably between 20 and 40 bar.

In some cases, hydrocarbon-containing feed gas may be subjected to prereforming before being provided to the reforming reactor. For example, when the hydrocarbon-containing feed gas is e.g. an LPG and/or a naphtha product stream or a natural gas feed, a prereforming unit may be arranged upstream the reforming reactor, and the method may further comprise the step of prereforming a hydrocarbon feed together with a steam feedstock in the prereforming unit to provide the hydrocarbon-containing feed gas.

In some cases, the hydrocarbon-containing feed gas may contain minor amount of poisons, such as sulfur. In this case, the hydrocarbon-containing feed gas may be subjected to one or more steps of purification such as desulfurization. Therefore, a gas purification unit may be arranged upstream the prereforming unit, and the method may further comprise the step of purifying a raw hydrocarbon feed in said gas purification unit to provide hydrocarbon-containing feed gas.

In a further step (b) of the method, the hydrocarbon-containing feed gas is reformed in the reforming reactor, to provide a first synthesis gas stream. The reforming reactor may comprise a tubular reformer, a convective reformer, an electrically heated reformer, an autothermal reformer, a partial oxidation (PDX) reformer or a combination thereof, in particular, a combination of a tubular reformer placed in series with an autothermal reformer, or a combination of an electrically heated reformer placed in series with an autothermal reformer.

The operating pressure of the reforming reactor will typically be between 5 and 50 bars or more preferably between 15 and 40 bars. The temperature of the gas exiting the reforming reactor is typically between 900 and 1150° C.

A typical tubular reformer consists of a number of tubes filled with catalyst pellets placed inside a furnace. The tubes are typically 10-13 meters long and will typically have an inner diameter between 80 and 160 mm. Burners placed in the furnace provide the required heat for the reactions by combustion of a fuel gas. A maximum average heat flux of 80000-90000 kcal/h/m 2 of inner tube surface is not uncommon. There is a general limitation to the obtainable heat flux due to mechanical constraints and the capacity is therefore increased by increasing the number of tubes and the furnace size. More details on the tubular reformer type reforming reactor can be found in the art, e.g. "Synthesis gas production for FT synthesis"; Chapter 4, p. 258-352, 2004.

Autothermal Reformer (ATR)

An autothermal reformer typically comprises a burner, a combustion chamber, and a catalyst bed contained within a refractory lined pressure shell. In an ATR, partial combustion of the hydrocarbon containing feed by sub-stoichiometric amounts of oxygen is followed by steam reforming of the partially combusted hydrocarbon-containing feed gas in a fixed bed of steam reforming catalyst. Steam reforming also takes place to some extent in the combustion chamber due to the high temperature. The steam reforming reaction is accompanied by the water gas shift reaction. Typically, the gas is at or close to equilibrium at the outlet of the reactor with respect to steam reforming and water gas shift reactions. More details of ATR and a full description can be found in the art such as "Studies in Surface Science and Catalysis, Vol. 152," Synthesis gas production for FT synthesis"; Chapter 4, p. 258-352, 2004".

In the case where the reforming reactor comprises an autothermal reformer, an $O_2$ containing feed is provided to said autothermal reformer. The $O_2$-containing feed is advantageously substantially pure $O_2$, such as >90% pure, preferably >95% pure, and even more preferably >99% pure.

Typically, the effluent gas from an ATR has a temperature of 900-1100° C. The effluent gas normally comprises $H_2$, CO, $CO_2$, and steam. Other components such as methane, nitrogen, and argon may also be present often in minor amounts. The operating pressure of the ATR reactor will be between 5 and 50 bars or more preferably between 15 and 40 bars.

Electrically Heated Reformer (e-SMR)

In one preferred aspect, the reforming reactor comprises or consists of an electrically heated reformer. The electrically heated steam methane reformer (eSMR) is a very compact steam reforming reactor which is an advantage especially for smaller scale plants.

The electrically heated reformer preferably comprises a pressure shell housing a structured catalyst, wherein the structured catalyst comprises a macroscopic structure of an electrically conductive material. The macroscopic structure supports a ceramic coating, where said ceramic coating supports a catalytically active material. The reforming step in this aspect comprises the additional step of supplying electrical power via electrical conductors connecting an electrical power supply placed outside said pressure shell to said structured catalyst, allowing an electrical current to run through said macroscopic structure material, thereby heating at least part of the structured catalyst to a temperature of at least 500° C.

Suitably, the electrical power supplied to the electrically heated reformer is generated by means of a renewable energy source.

The structured catalyst of the electrically heated reformer is configured for steam reforming. This reaction takes place according to the following reactions:

$$CH_4+H_2 \leftrightarrow CO+3H_2$$

$$CH_4+2H_2O \leftrightarrow CO_2+4H_2$$

$$CH_4+CO_2 \leftrightarrow 2CO+2H_2$$

The structured catalyst is composed a metallic structure, a ceramic phase, and an active phase. The metallic structure may be FeCrAlloy, Alnico, or similar alloys. The ceramic phase may be $Al_2O_3$, $MgAl_2O_3$, $CaAl_2O_3$, $ZrO_2$, or a combination thereof. The catalytically active material may be Ni, Ru, Rh, Ir, or a combination thereof.

In an embodiment, catalyst pellets are loaded on top of, around, inside, or below the structured catalyst of the reforming reactor. The catalyst material for the reaction may be $Ni/Al_2O_3$, $Ni/MgAl_2O_3$, $Ni/CaAl_2O_3$, $Ru/MgAl_2O_3$, or $Rh/MgAl_2O_3$. The catalytically active material may be Ni, Ru, Rh, Ir, or a combination thereof. This can improve the overall gas conversion inside the electrically heated reformer.

In an embodiment, the macroscopic structure(s) has/have a plurality of parallel channels, a plurality of non-parallel channels and/or a plurality of labyrinthic channels. The channels have walls defining the channels. Several different forms and shapes of the macroscopic structure can be used as long as the surface area of the structured catalyst exposed to the gas is as large as possible.

In an embodiment, the macroscopic structure(s) is/are extruded and sintered structures. Alternatively, the macroscopic structure(s) is/are 3D printed structure(s). A 3D printed structure can be provided with or without subsequent sintering. Extruding or 3D printing a macroscopic structure, and optional subsequent sintering thereof results in a uniformly and coherently shaped macroscopic structure, which can afterwards be coated with the ceramic coating.

A ceramic coating, which may contain the catalytically active material, is provided onto the macroscopic structure before a second sintering in an oxidizing atmosphere, in order to form chemical bonds between the ceramic coating and the macroscopic structure. Alternatively, the catalytically active material may be impregnated onto the ceramic coating after the second sintering.

As used herein, the terms “3D print” and “3D printing” is meant to denote a metal additive manufacturing process. Such metal additive manufacturing processes cover 3D printing processes in which material is joined to a structure under computer control to create a three-dimensional object, where the structure is to be solidified, e.g. by sintering, to provide the macroscopic structure. Moreover, such metal additive manufacturing processes cover 3D printing processes, which do not require subsequent sintering, such as powder bed fusion or direct energy deposition processes. Examples of such powder bed fusion or direct energy deposition processes are laser beam, electron beam or plasma 3D printing processes.

Preferably, the catalytically active material is particles having a size from 5 nm to 250 nm. The ceramic coating may for example be an oxide comprising Al, Zr, Mg, Ce and/or Ca. Exemplary coatings are calcium aluminate or a magnesium aluminum spinel. Such a ceramic coating may comprise further elements, such as La, Y, Ti, K or combinations thereof. Preferably, the conductors are made of different materials than the macroscopic structure. The conductors may for example be of iron, nickel, aluminum, copper, silver or an alloy thereof. The ceramic coating is an electrically insulating material and will typically have a thickness in the range of around 100 μm, e.g. about 10-500 μm.

In an optional step b1) at least part of the first synthesis gas stream from step b) is fed to a water gas shift reactor to provide shifted synthesis gas stream according to the following reactions and thermodynamic constraints:

$$H_2O+CO \leftrightarrow CO_2+H_2$$

The skilled person can select suitable water gas shift reactors and operating conditions as required. In one aspect, the entirety of the first synthesis gas stream from step b) is fed to the water gas shift reactor and shifted. In another aspect, only a first part of the first synthesis gas stream from step b) is fed to the water gas shift reactor and shifted, and a second part of the first synthesis gas stream is fed to the cooling unit in the subsequent step together with the shifted synthesis gas stream. In other aspects, additional steam is added to the first synthesis gas stream from step b) and is fed to the water gas shift reactor and shifted. Use of the water gas shift step allows the $H_2/CO$ ratio in the first synthesis gas stream to be adjusted as required for downstream processes.

In a further step (c) of the method, the first synthesis gas stream and/or the shifted synthesis gas stream is cooled in a cooling unit, to provide a second synthesis gas stream. Preferably, all synthesis gas, i.e. both the first and synthesis gas stream and the shifted synthesis gas stream, is cooled in said cooling unit.

The first synthesis gas stream typically exits the reforming reactor at a temperature of between 800° C. and 1200° C. The cooling unit reduces the temperature in the second synthesis gas stream to below the condensation point of the water in the stream, such as to between 30° C. and 50° C. The cooling unit may comprise more than one cooling stage, e.g. two cooling stages, arranged in series.

In a further step (d) of the method, water is removed from the second synthesis gas stream in a water removal unit. This is advantageously done by flash separation, to provide a third synthesis gas stream. By flash separation is meant a phase separation unit, where a stream is divided into a liquid and gas phase close to or at the thermodynamic phase equilibrium at a given temperature.

In a further step (e) of the method, the third synthesis gas stream is compressed in a compressing unit to a first pressure, said first pressure being higher than the feed pressure of said hydrocarbon feed gas, to provide a fourth synthesis gas stream. Typically, the first pressure to which the third synthesis gas stream is compressed lies between 50 and 150 barg, preferably between 80 and 90 barg. In contrast, the feed pressure of the hydrocarbon feed gas (and the third synthesis gas stream) is typically between 20 and 50 barg, preferably between 25 and 35 barg. The compressor unit may comprise two or more compressors arranged in series. In the configuration of the invention, the same compressor unit facilitates downstream $CO_2$ removal and methanol synthesis, allowing these operations to be performed without intermediate compression.

The method may—optionally— comprise a step (e1) of feeding at least part of the fourth synthesis gas stream from step e) to a $CO_2$ removal unit, to thereby provide at least a $CO_2$-rich stream and a fifth synthesis gas stream. By $CO_2$ removal is meant a process for separating $CO_2$ from the process gas. $CO_2$ removal may be facilitated by methods such as $CO_2$ absorption, membrane, or cryogenic separation. Generally, methods for $CO_2$ removal are favored at elevated pressure.

In a specific embodiment, the $CO_2$ removal unit is a cryogenic separation unit. Typically, cryogenic separation utilizes the phase change of different species in the gas to separate individual components (i.e. $CO_2$) from a gas mixture by controlling the temperature, typically taking place below −50° C. Such a cryogenic separation unit typically comprises a first cooling stage of the synthesis gas, followed by cryogenic flash separation unit to separate the liquid condensate from the gas phase. Cooling for the first cooling stage may be provided by the resulting product from the cryogenic flash separation unit, potentially in the combination with other coolants. Optionally, one or more of the products from the $CO_2$ removal unit may be expanded to some extent to make a colder process gas for this cooling stage. Cryogenic separation of $CO_2$ must be facilitated at elevated pressure, at least above the triple point of $CO_2$ to allows condensation of $CO_2$. A suitable pressure regime is therefore at least above the triple point of 5 bar, where increased pressure gives increased liquid yields.

By $CO_2$ absorption is meant a unit utilizing a process, such as chemical absorption, for removing $CO_2$ from the process gas. In chemical absorption, the $CO_2$ containing gas is passed over a solvent which reacts with $CO_2$ and in this way binds it. The majority of the chemical solvents are amines, classified as primary amines as monoethanolamine (MEA) and digylcolamine (DGA), secondary amines as diethanolamine (DEA) and diisopropanolamine (DIPA), or tertiary amines as triethanolamine (TEA) and methyldiethanolamine (MDEA), but also ammonia and liquid alkali carbonates as $K_2CO_3$ and $NaCO_3$ can be used.

By membrane is meant separation over an at least partly solid barrier, such as a polymer, where the transport of individual gas species takes place at different rates defined by their permeability. This allows for up-concentration, or dilution, of a component in the retentate of the membrane.

The $CO_2$-rich stream (or $CO_2$-rich condensate when the $CO_2$ removal unit is a cryogenic separation unit) is typically rich in $CO_2$, such as >80% pure, preferably >90% pure. Further purity can prospectively be achieved by distillation or other purification techniques if needed.

In a further step (f) of the method, at least part of the fourth synthesis gas stream and/or at least part of the fifth synthesis gas stream (where present) is/are fed to a methanol synthesis unit. A methanol-rich stream is provided in said methanol synthesis unit from the fourth and/or fifth synthesis gas stream(s).

By the term "methanol synthesis unit" is understood one or several reactors configured to convert a synthesis gas into methanol. Such reactors can for example be a boiling water reactor, an adiabatic reactor, a condensing methanol reactor or a gas-cooled reactor. Moreover, these reactors could be many parallel reactor shells and sequential reactor shells with intermediate heat exchange and/or product condensation. It is understood that the methanol synthesis unit also contains equipment for recycling and pressurizing feed to the methanol reactor(s) in configurations where this is found advantageous.

In one preferred aspect, a first part of the fourth synthesis gas stream from step e) is fed to the $CO_2$ removal unit, to provide the $CO_2$-rich stream and the fifth synthesis gas stream. A second part of the fourth synthesis gas stream is not fed to the $CO_2$ removal unit. At least part of the fifth synthesis gas stream (from the $CO_2$ removal unit) is fed to the methanol synthesis unit together with a second part of the fourth synthesis gas stream. By adjusting the proportion of the fourth synthesis gas stream which is fed to the $CO_2$ removal unit, vs. the proportion which is fed directly to the methanol synthesis unit, the molar ratio between the methanol product stream and the hydrogen product stream can be adjusted. Typically, if the proportion of the fourth synthesis gas stream fed to the $CO_2$ removal unit is increased, the relative amount of methanol product stream decreases compared to the hydrogen product stream. This allows for shifting the ratio between the $H_2$ and methanol product from the plant, and consequently increases the agility of the plant according to production demands.

In a further step (g), at least part of the methanol-rich stream from step f) is fed to a separation unit. The methanol-rich stream is separated in the separation unit to provide a methanol product stream and a hydrogen rich stream. The separation unit is advantageously a flash separation unit. Often the methanol product stream will subsequently be expanded and any adsorbed gas species in the gas will evaporate, a second separation stage with a low-pressure flash separation unit is advantageously done also to provide a low-pressure methanol product stream.

The methanol product stream which can be obtained from the separation unit is more than 90% methanol, preferably more than 95% methanol. Other minor components include water and $CO_2$, and prospective byproducts from the methanol synthesis such as acetone and ethanol. The methanol product stream can be upgraded to a higher quality methanol product stream, e.g. more than 98% or more than 99% methanol. The methanol product stream can be utilised in the production of other useful product streams e.g. gasoline, jet fuel, formaldehyde, acetic acid or ethylene. The method may further comprise the step of converting at least part of the methanol product stream to transportation fuel. In an embodiment, the method further comprises the step of upgrading the methanol product stream to fuel grade (i.e.

>80%) methanol. In an embodiment, the methanol product stream is upgraded to chemical grade (i.e. >99%) methanol.

Upgrading the methanol product stream typically provides an off-gas stream comprising alcohols, ketones and other prospective by-product from methanol synthesis. This off-gas stream can be recycled and used as e.g. fuel for heating one or more units located upstream in the method/system of the invention. Part of this off-gas stream may alternatively constitute part of the hydrocarbon containing feed gas. This off-gas stream may also be combined with the off-gas stream from the $H_2$ purification unit (see below).

In a further optional step (h), at least part of the hydrogen rich stream from step g) is provided to a $H_2$ purification unit. The $H_2$ purification unit separates the hydrogen rich stream into a hydrogen product stream and an off-gas stream. The $H_2$ purification unit is suitably a pressure-swing absorption (PSA) unit, a membrane unit or a cryogenic separation unit. The hydrogen product stream which can be obtained from the $H_2$ purification unit is more than 95% hydrogen, preferably more than 98% hydrogen, even more preferably more than 99% hydrogen. Other minor components include nitrogen. The hydrogen product stream can be upgraded to a higher quality hydrogen product stream, e.g. more than 99.5% or more than 99.9% hydrogen. When using a PSA, the hydrogen product can be delivered at almost the same pressure as the hydrogen rich stream from step g). In such an embodiment, the method of the invention allows for configuring a chemical plant which produces $CO_2$ at elevated pressure (such as above barg) and $H_2$ at elevated pressure (such as above 50 barg), while at the same time having an outlet of liquid methanol. This makes further processing of each of the outlet advantageous as it makes transfer and integration easier.

The off-gas stream from the $H_2$ purification unit comprises a mixture of $CO_2$, $CH_4$, $H_2$ and CO, with minor amounts of $N_2$ and methanol. This off-gas stream can be recycled and used as e.g. fuel for heating one or more units located upstream in the method/system of the invention.

The remaining part of the hydrogen rich stream from step g) which is not used for hydrogen production can advantageously be compressed and returned to the methanol synthesis unit (50) (step f) as a methanol loop recycle stream. By changing the relative part between the hydrogen rich stream and the methanol loop recycle stream, the relative production of $H_2$ and methanol can be changed. Having a relative high proportion of methanol loop recycle stream gives a relative lower production of hydrogen but an increased production of methanol.

The method and the system of the invention allow adjusting the molar ratio between the hydrogen product stream and the methanol product stream, and the method may further comprise the step of adjusting the molar ratio between the hydrogen product stream and the methanol product stream. For instance, from a ratio in the range of 2.5-5, to a ratio in the range of 1-2.5, or vice-versa. In an embodiment the ratio between hydrogen product stream and the methanol product stream is changed from 3.5 to 2.5. In another embodiment the ratio is changed from 2.0 to 2.8. In a third embodiment the ratio is changed from 2.8 to 1.8. The ratio can conceivably also be changed in smaller steps, such as from 3.8 to 3.0, or vice-versa. Or such from 2.0 to 2.3, or vice-versa.

One way to adjust this ratio is by adjusting the proportion of the fourth synthesis gas stream which is fed to the $CO_2$ removal unit, as above.

Another way to adjust this ratio is to adjust the amount of $CO_2$ which is condensed in the $CO_2$ removal unit, relative to the $CO_2$ content in the fourth synthesis gas stream. By increasing the amount of $CO_2$ which is condensed in the $CO_2$ removal unit, relative to the $CO_2$ content in the fourth synthesis gas, the molar ratio between the methanol product stream and the hydrogen product stream decreases. An increase in the amount of $CO_2$ condensed in the $CO_2$ removal unit may be achieved by decreasing the operating temperature in the $CO_2$ removal unit. The relevant operating regime of a $CO_2$ removal unit in the form of a cryogenic separation unit is from ca. −30° C. to −80° C.

Another way to adjust this ratio is to adjust the amount of the first synthesis gas which is fed to the water gas shift reactor. When increasing the relative amount of the shifted synthesis gas stream, the molar ratio between the methanol product stream and the hydrogen product stream decreases.

In one aspect, the method of the invention further comprises the step of providing a $CO_2$-containing feed to the reforming reactor, preferably in admixture with said hydrocarbon-containing feed gas. In this manner, the $CO_2$-containing feed may be regulated such that the module of said first synthesis gas stream is in a suitable range e.g. in the range of 1.5 to 2.5. In an embodiment the $CO_2$-containing feed is at least partly supplied by the $CO_2$ condensed in the $CO_2$ removal unit. The $CO_2$-containing feed may also, at least partly, be supplied by offgas from the methanol upgrading unit.

In the case where the reforming reactor comprises an autothermal reformer, and where an $O_2$-containing feed is provided to said autothermal reformer, the method may further comprise the step of regulating the $O_2$-containing feed such that the module of said first synthesis gas stream is in the range of 1.5 to 2.5. This provides an alternative—or additional—method for adjusting the module of the first synthesis gas stream to the preferred range for methanol synthesis.

The method may further comprise the step of providing an $H_2$-containing feed, upstream the methanol synthesis unit. The $H_2$-containing feed is preferably a feed of substantially pure (i.e. >99%) $H_2$. $H_2$-containing feed is preferably fed to the methanol synthesis unit in admixture with the at least part of the fourth synthesis gas stream and/or at least part of the fifth synthesis gas stream. Alternatively, the $H_2$-containing feed is fed to the hydrocarbon-containing feed gas.

Advantageously, the $H_2$-containing feed is fed to the compressing unit in admixture with third synthesis gas stream. Such an arrangement can avoid pre-compression of the $H_2$-containing feed and provides a combined fourth synthesis gas stream with the required module and at the required pressure.

The $H_2$-containing feed may also be supplied to the hydrocarbon-containing feed gas and used as the reducing gas requirement for the hydrocarbon containing feed gas.

The method may further comprise the step of regulating the $H_2$-containing feed such that the module of said fourth and/or fifth synthesis gas stream is in the range of 1.5 to 2.5. The module is determined at the inlet of the methanol synthesis unit.

The molar ratio between the methanol product stream and the hydrogen product stream may also be changed by regulating the $CO_2$-containing feed, the $O_2$-containing feed, and/or the $H_2$-containing feed. Increasing the $CO_2$-containing feed will increase the relative production of the methanol product stream relative to the hydrogen product stream. Increasing the $O_2$-containing feed will increase the methanol product stream relative to the hydrogen product stream. Increasing the $H_2$-containing feed will increase the hydrogen product stream relative to the methanol product stream.

In one particular aspect of the method, an electrolysis unit is provided. The method further comprises the step of generating an $H_2$-containing feed and an $O_2$-containing feed in the electrolysis unit from a water feedstock, and the method further comprises the step(s) of supplying at least a part of said $H_2$-containing feed to the methanol synthesis unit and/or supplying at least a part of said $O_2$-containing feed to the autothermal reformer. Including such an electrolysis unit allows $H_2$ and $O_2$ to be readily provided, while avoiding the use of fossil-fuels. In a preferred embodiment, the electrolysis unit is a solid oxide electrolysis cell.

In an embodiment, the electrolysis unit is a high temperature electrolysis unit, such as a solid oxide electrolysis cell type, and the water feedstock for the electrolysis unit is in the form of steam produced from other processes of the method. For instance, steam is generated in the methanol synthesis unit and/or the cooling unit for the first synthesis gas.

In one aspect, the invention provides a system for upgrading a hydrocarbon-containing feed gas to a methanol product stream and a hydrogen product stream. All structural features provided above in respect of the method of the invention are also relevant for the system of the invention.

In general terms, the system comprises:

- a hydrocarbon-containing feed gas arranged to be fed to a reforming reactor,
- reforming reactor arranged to reform said hydrocarbon-containing feed gas; to thereby provide a first synthesis gas stream from the reforming reactor,
- optionally, a water gas shift reactor arranged to receive at least part of the first synthesis gas stream from the reforming reactor and provide shifted synthesis gas stream,
- a cooling unit arranged to cool said first synthesis gas stream and/or the shifted synthesis gas stream and thereby provide a second synthesis gas stream,
- a water removal unit arranged to remove water from said second synthesis gas stream, and thereby provide a third synthesis gas stream,
- a compressing unit arranged to compress said third synthesis gas stream to a first pressure, said first pressure being higher than the feed pressure of said hydrocarbon feed gas, and thereby provide a fourth synthesis gas stream,
- optionally, a $CO_2$ removal unit, arranged to receive at least a part of the fourth synthesis gas stream and to provide a $CO_2$-rich stream and a fifth synthesis gas stream,
- a methanol synthesis unit arranged to convert at least part of the fourth synthesis gas stream and/or at least part of the fifth synthesis gas stream to a methanol-rich stream,
- a separation unit, arranged to provide a methanol product stream and a hydrogen rich stream from at least part of the methanol-rich stream,
- optionally, an $H_2$ purification unit, arranged to separate said hydrogen-rich stream into a hydrogen product stream and an off-gas stream.

All details of the units and reactors in the system of the invention are as described above for the method of the invention.

In one aspect of the system, a first part of the fourth synthesis gas stream is arranged to be fed to the $CO_2$ removal unit, to provide the $CO_2$-rich stream and the fifth synthesis gas stream; and wherein at least part of the fifth synthesis gas stream is arranged to be fed to said methanol synthesis unit together with a second part of the fourth synthesis gas stream. A system arranged in this manner allows easy regulation of the composition of the synthesis gas stream at the inlet of the methanol synthesis unit.

In another aspect, the system further comprises a $CO_2$-containing feed arranged to be fed to said reforming reactor, preferably in admixture with said hydrocarbon-containing feed gas. The presence of this $CO_2$ feed allows the module of the synthesis gas stream to be regulated as required.

The system may additionally comprise an autothermal reformer. In this case, the system further comprises an $O_2$-containing feed arranged to be fed to said autothermal reformer.

The system may further comprise an $H_2$-containing feed arranged to be fed upstream the methanol synthesis unit, preferably in admixture with the at least part of the fourth synthesis gas stream and/or at least part of the fifth synthesis gas stream.

Thus, the molar ratio between the methanol product stream and the hydrogen product stream can be changed by regulating the $CO_2$-containing feed, the $O_2$-containing feed, and/or the $H_2$-containing feed.

As above for the method, the system according to the invention may further comprise an electrolysis unit, said electrolysis unit being arranged to generate an $H_2$-containing feed and an $O_2$-containing feed from a water feedstock, said system being further arranged to supply said $H_2$-containing feed from said electrolysis unit to the methanol synthesis unit and/or supply said $O_2$-containing feed from said electrolysis unit to the autothermal reformer (when present).

The reforming reactor may comprise a tubular reformer, a convective reformer, an electrically heated reformer, an autothermal reformer, or a combination thereof, in particular, a combination of a tubular reformer placed in series with an autothermal reformer, or a combination of an electrically heated reformer placed in series with an autothermal reformer.

In particular, the reforming reactor may be an electrically heated reformer. The electrically heated reformer suitably comprises a pressure shell housing a structured catalyst, wherein said structured catalyst comprises a macroscopic structure of an electrically conductive material, said macroscopic structure supporting a ceramic coating, where said ceramic coating supports a catalytically active material; and wherein electrical conductors connecting an electrical power supply are placed outside said pressure shell and arranged to supply electrical power to said structured catalyst, thereby allowing an electrical current to run through said macroscopic structure material, and thereby heating at least part of the structured catalyst to a temperature of at least 500° C.

The $H_2$ purification unit is suitably a pressure-swing absorption (PSA) unit, a membrane unit or a cryogenic separation unit. The separation unit is suitably a flash separation unit.

The system according to the invention may comprise a prereforming unit, located upstream the reforming reactor and arranged to pre-reform the hydrocarbon-containing feed gas. Similarly, the system may comprise a gas purification unit, located upstream the pre-reforming reactor and arranged to purify a raw hydrocarbon-containing feed gas.

The following is a detailed description of embodiments of the invention depicted in the accompanying drawings. The embodiments are examples and are in such detail as to clearly communicate the invention. However, the amount of detail offered is not intended to limit the anticipated variations of embodiments; but on the contrary, the intention is to cover all modifications, equivalents, and alternatives falling within the spirit and scope of the present invention as defined by the appended claims.

DETAILED DESCRIPTION OF THE DRAWINGS

FIG. 1 is a schematic drawing of a system for upgrading of hydrocarbon-containing feed gas 1 to a methanol product stream 61 and a hydrogen product stream 71.

In the shown embodiment, the hydrocarbon-containing feed gas 1 is prepared upstream the figure in a predefined ratio of steam, hydrocarbons, and other constituents from the feedstocks. This is fed to a reforming reactor 10 to facilitate steam reforming which provides a first synthesis gas stream 11. The central function of the reforming reactor is to increase the temperature of the gas, preferably to temperatures in the range from 800-1200° C., e.g. around 1000° C., while facilitating the endothermic steam reforming reactions to enable conversion of the hydrocarbon-containing feed gas into a first synthesis gas comprising at least CO and $H_2$. In the shown embodiment, the system comprises an electrically heated steam methane reformer (eSMR) 10, although other reforming reactors are possible. The first synthesis gas stream 11 is cooled in a cooling unit 20; only one heat exchanger is shown in the current embodiment, but many heat exchangers are conceivable. The cooling unit 20 cools the hot first synthesis gas stream 11, preferably to a temperature below the dew point of the stream, such as between 30 and 50° C. In the embodiment of FIG. 1, this provides a two-phase stream as the second synthesis gas stream 21. The condensate of the second synthesis gas stream 21 can in this way be removed in a water removal unit 30, which in the current embodiment is a flash separation unit. In this configuration the principal part of the water from then synthesis gas can be removed and typically the content of water in the third synthesis gas is below 1%.

The third synthesis gas stream 31 is then compressed in a compressing unit 40 to a pressure being higher than the feed pressure of said hydrocarbon feed gas 1. Compressing unit 40 provides a fourth synthesis gas stream 41. As above, the pressure of the fourth synthesis gas stream typically lies between 50 and 150 barg, preferably between 80 and 90 barg. In contrast, the feed pressure of the hydrocarbon feed gas (and the third synthesis gas stream) is typically between 20 and 40 barg, preferably between and 35 barg.

The fourth synthesis gas stream 41 may be heated further in a heat exchanger prior to being fed to methanol synthesis unit 50 to achieve sufficient activity in the unit.

In the system of FIG. 1, the fourth synthesis gas stream 41 is fed to the methanol synthesis unit 50. A methanol-rich stream 51 (typically 20-30% methanol content) is outputted from the methanol synthesis unit.

At least a part of the methanol-rich stream 51 (and preferably the entirety of this stream) is fed to a separation unit 60. Separation unit 60 is arranged to provide a methanol product stream 61 and a hydrogen rich stream 62 from at least part of the methanol-rich stream 51. In the system of FIG. 1, the separation unit 60 is a flash separation unit.

At least part of the hydrogen rich stream 62 from the separation unit is fed to a $H_2$ purification unit 70 (which may be a pressure-swing absorption (PSA) unit, a membrane unit or a cryogenic separation unit). In the $H_2$ purification unit, the hydrogen rich stream 62 is separated into a hydrogen product stream 71 and an off-gas stream 72.

Figure 2:
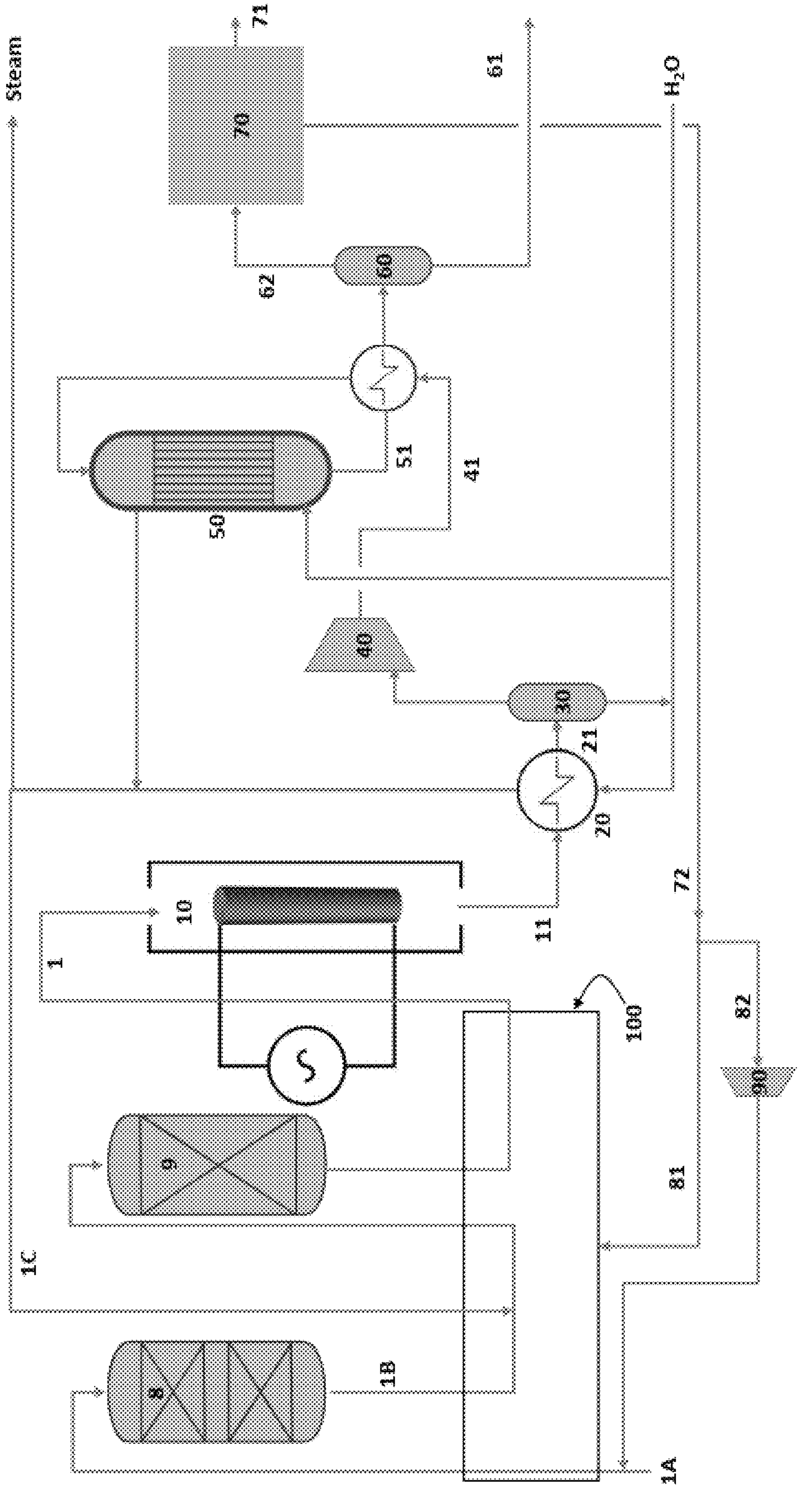
FIG. 2 is a schematic drawing of a system similar to FIG. 1, further including a pre-reforming unit and a gas purification unit.

The system illustrated in FIG. 2 comprises all elements of FIG. 1, plus a gas purification unit 8, e.g. a desulfurization unit, and a prereformer 9. A preheating section 100 is also present to heat the various feed gases prior to reforming.

A hydrocarbon feed 1A is preheated in the preheating section 100 and is led to the gas purification unit 8. A purified preheated hydrocarbon feed 1B is sent from the gas purification unit 8 back to the preheating section 100 for further heating. Moreover, steam 1C is added to the purified preheated hydrocarbon feed 1B, and the resulting mixture is sent to the prereformer 9. Prereformed gas 1 exits the prereformer 9 and is again heated in the preheating section 100, resulting in hydrocarbon-containing feed gas 1 which is then fed to the eSMR 10.

As also illustrated in FIG. 2, at least part of the off-gas stream 72 from the $H_2$ purification unit 70 is recycled as a fuel supply for heating the preheating section and/or the e-SMR 10. The portion used as fuel 81 can be mixed with air to heat the preheating section 100. The part recycled to the hydrocarbon containing feed 82 may be compressed by means of compression 90 to achieve suitable mixing pressures.

Figure 3:
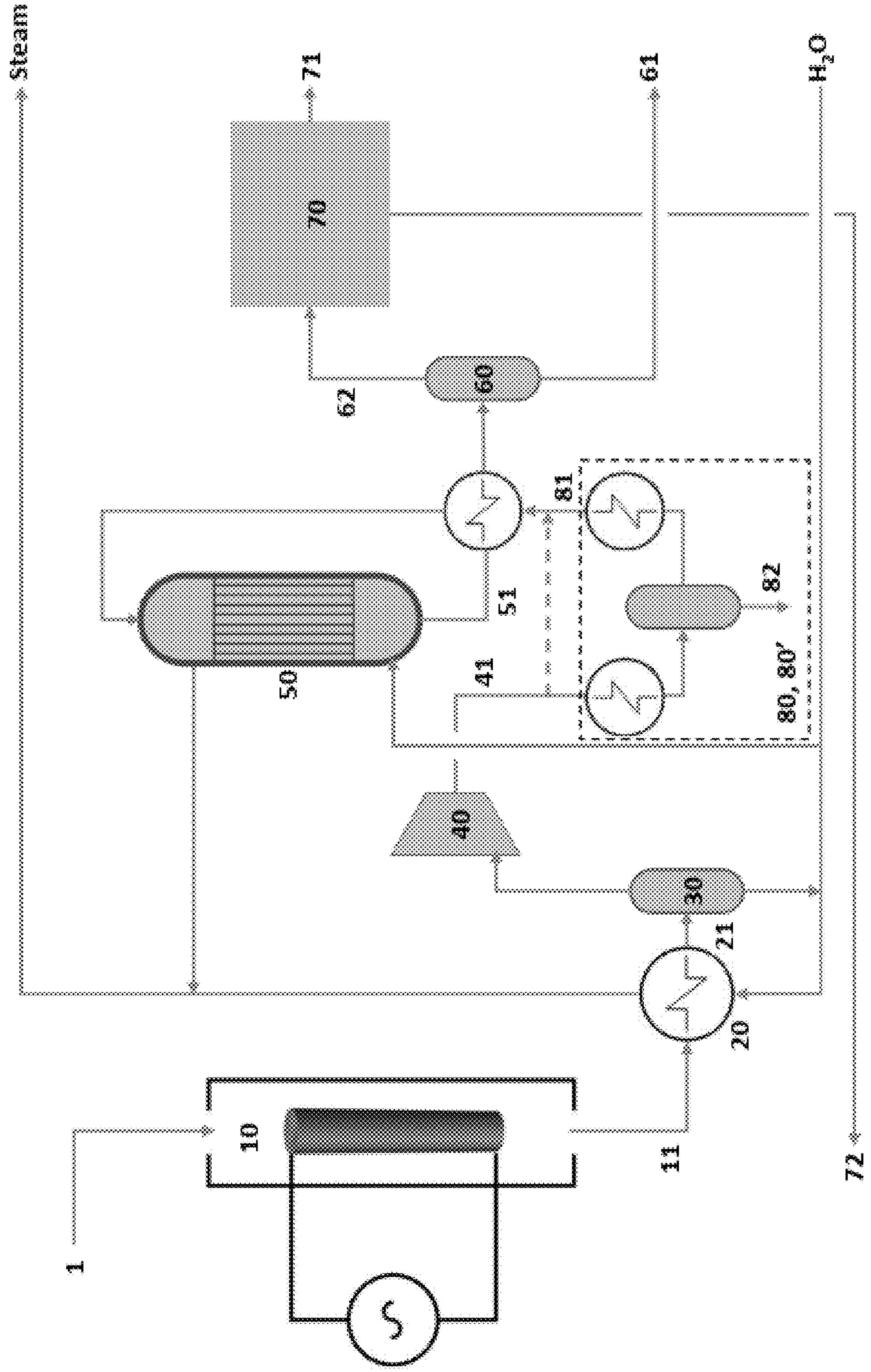
FIG. 3 is a schematic drawing of a system similar to FIG. 1, further including a $CO_2$ removal unit located between the compressing unit and the methanol synthesis unit.

The system illustrated in FIG. 3 comprises all elements of FIG. 1, plus a $CO_2$ removal unit 80 in the form of a cryogenic separation unit 80', located between the compressing unit 40 and the methanol synthesis unit 50. In FIG. 3, at least part of the fourth synthesis gas stream 41 from the compressing unit 40 is fed to the cryogenic separation unit 80'. In the embodiment of FIG. 3, the cryogenic separation unit comprises a cooling unit, followed by a flash separation unit, followed by a heating unit.

The output of the cryogenic separation unit is a $CO_2$-rich stream 82 and a fifth synthesis gas stream 81. The $CO_2$-rich stream 82 typically comprises substantially pure $CO_2$. At the separation point shown in FIG. 3, the $CO_2$ will be in liquid phase at high pressure suitable for integration with other parts of the process.

The fifth synthesis gas stream 81 differs from the fourth synthesis gas stream 41 principally in terms of the $CO_2$ content. The $CO_2$ content of the fifth synthesis gas stream 81 is typically less than 10%.

In the system of FIG. 3, the methanol synthesis unit is arranged to convert at least part of the fourth synthesis gas stream 41 and/or at least part of the fifth synthesis gas stream 81 to a methanol-rich stream 51. Optionally, as shown by the dashed arrow in FIG. 3, a portion of the fourth synthesis gas stream 41 bypasses the cryogenic separation unit 80' and is mixed with the fifth synthesis gas stream 81. Mixed fourth 41 and fifth 81 synthesis gas streams are sent to the methanol synthesis unit 50 together. This allows the make-up of the (combined) synthesis gas stream fed to the methanol synthesis unit 50 to be adjusted as desired (and thereby adjusting the ratio of the two product streams).

Figure 4:
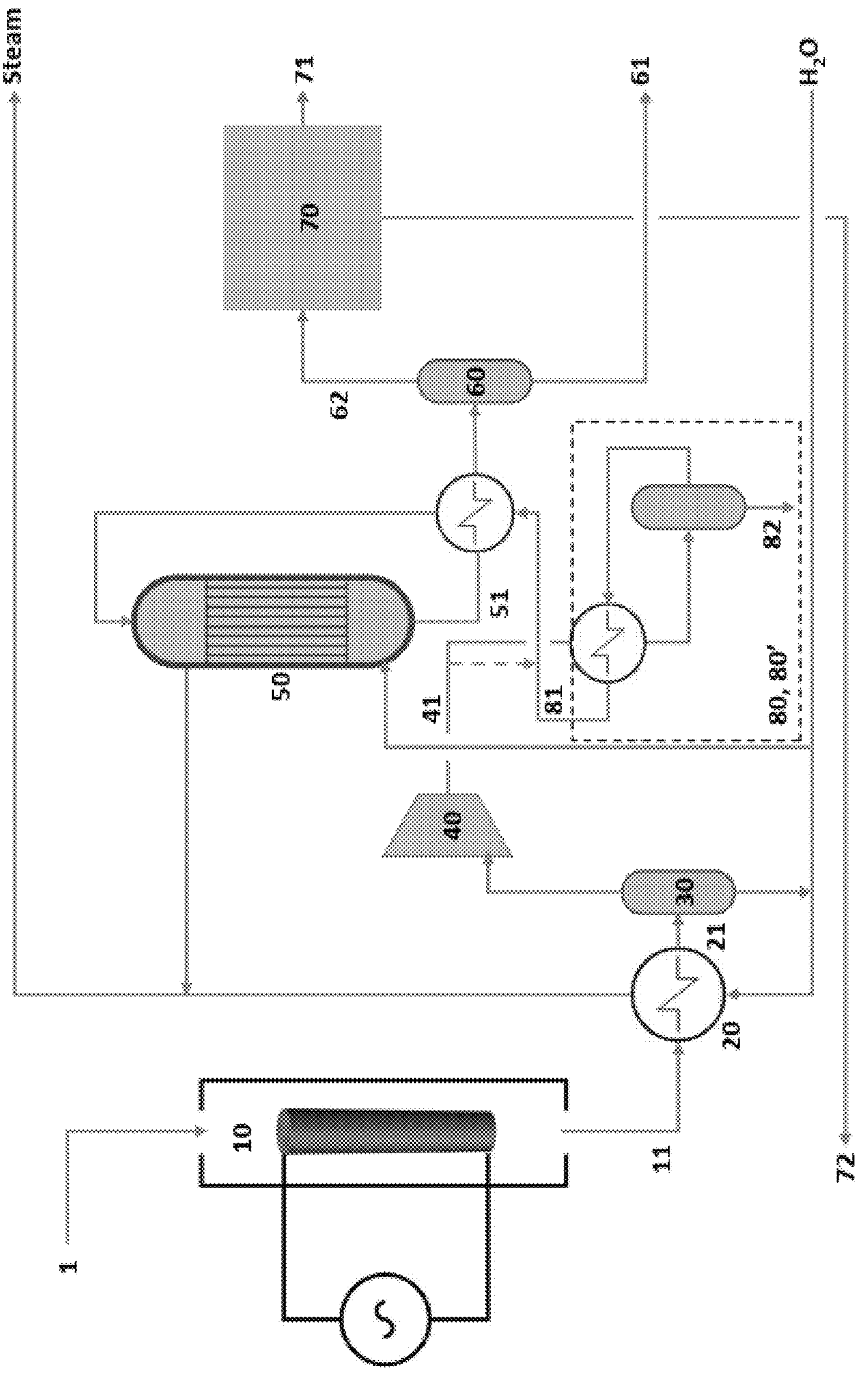
FIGS. 4 and 5 are schematic drawings of systems according to the invention.

The system illustrated in FIG. 4 comprises all elements of FIG. 3, but includes a different embodiment of the cryogenic separation unit 80' where the cooling and heating of the process gas is facilitated in a feed-effluent type of configuration. Notice that the cooling in this unit is insufficient for reaching the desired temperatures and additional or combined cooling with a supplementary stream would be needed.

Figure 5:
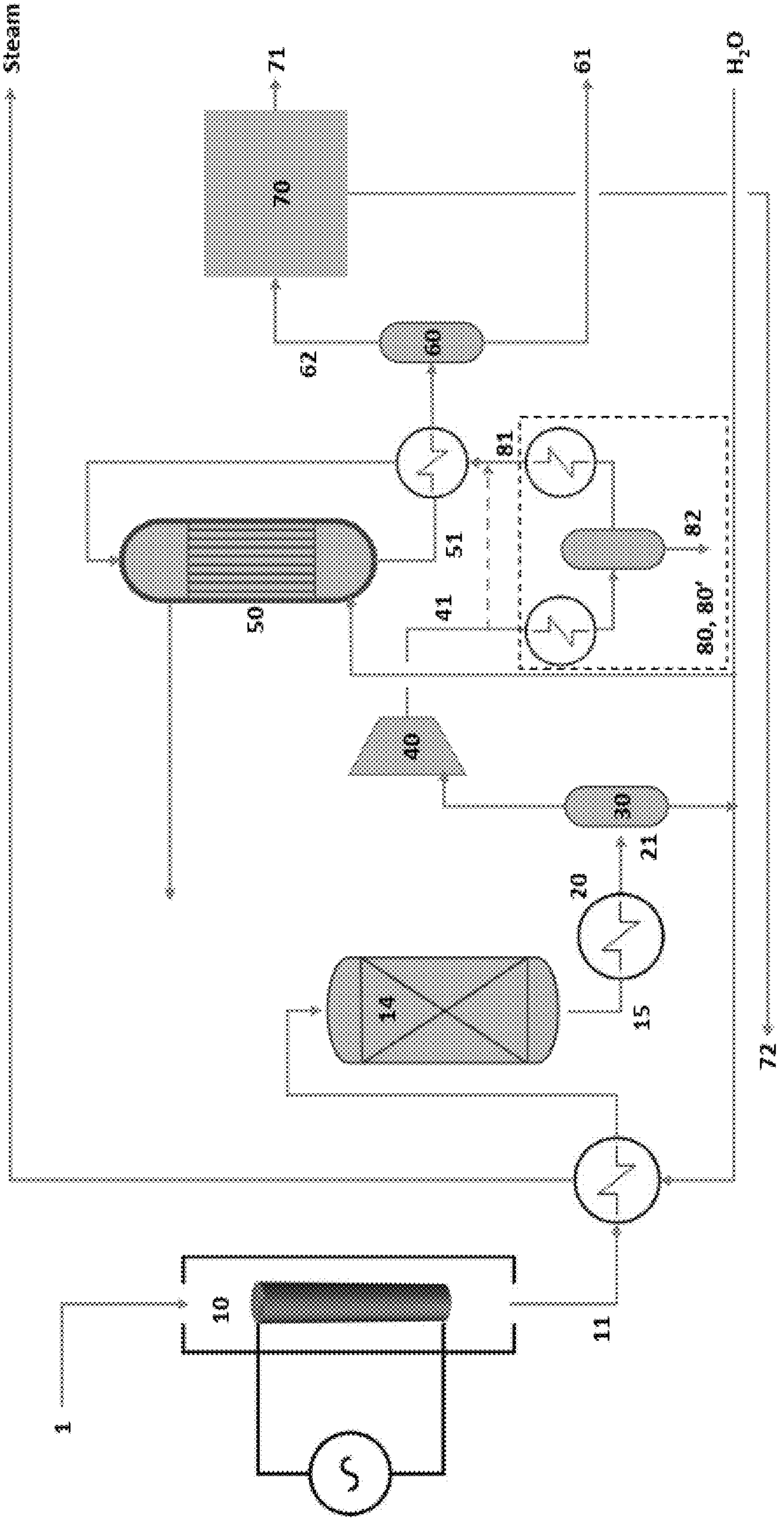

The system illustrated in FIG. 5 comprises all elements of FIG. 3, but also includes a water gas shift reactor 14 downstream the reforming reactor 10. In this embodiment the first synthesis gas is partly cooled to a temperature above the dewpoint of the gas and then reacted in a water gas shift reactor. In this way a substantial part of the CO in the synthesis gas is converted with $H_2O$ to $CO_2$ and $H_2$. This embodiment allows for an increased production of hydrogen relative to methanol from the system.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of applicant's general inventive concept.

Example 1

Table 1 and Table 2 shows process data from an example of the invention somewhat similar to the embodiment depicted in FIG. 5. A hydrocarbon-containing feed gas (1) is provided and reformed in a reforming reactor (10) to reach a temperature of 1015° C. at almost equilibrated conditions to provide a first synthesis gas (11). This is cooled and then shifted in a water gas shift reactor (14) to provide a shifted synthesis gas stream (15). This is cooled to 40° C. to provide a second synthesis gas stream (21). This temperature enforces a phase increase in the stream, and the water rich liquid condensate can subsequently be removed by flash separation (30) to provide a third synthesis gas stream (31). This is compressed to 88 barg in a compressing unit (40) to provide a fourth synthesis gas stream (41). Part of the $CO_2$ of this stream is removed in a cryogenic separation unit (80') to provide a fifth synthesis gas stream (81) and a $CO_2$ rich stream (82). In the used embodiment, the cryogenic separation unit (80') comprises several cooling and condensations steps to make sure suitable cooling without risk of freezing is facilitated. The fifth synthesis gas stream (81) is heated and converted in a boiling water type methanol reactor (50) to a methanol-rich stream (51). This is cooled to allow separation of the methanol in a liquid phase by flash separation (60), in this way providing a methanol product stream (61) and a hydrogen rich stream (62). The hydrogen rich stream (62) is purified in a PSA into a hydrogen product stream (71) and an off-gas stream (72).

This embodiment of the invention allows for producing a product split of 287 $Nm^3/h$ of $CO_2$ at a purity of 96% at 88 barg, 2109 $Nm^3/h$ of $H_2$ at a purity of 99.9% and 85 barg, and 566 $Nm^3/h$ $CH_3OH$ at a purity of 84% and 85 barg.

TABLE 1

| Stream ID | 1 | 11 | 15 | 21 | 31 | 41 | 81 |
|---|---|---|---|---|---|---|---|
| Temperature (° C.) | 403 | 1015 | 438 | 40 | 40 | 219 | −70 |
| Pressure (bar g) | 26.4 | 25.0 | 23.5 | 22.5 | 22.5 | 88.3 | 87.7 |
| Total Flow ($Nm^3/h$) | 2929 | 4716 | 4716 | 4716 | 4318 | 4320 | 4019 |
| Composition [mole %] | | | | | | | |
| Carbon Dioxide | 1.4 | 2.6 | 10.1 | 10.1 | 11.0 | 11.0 | 5.0 |
| Nitrogen | 0.5 | 0.3 | 0.3 | 0.3 | 0.4 | 0.4 | 0.4 |
| Methane | 33.2 | 1.6 | 1.6 | 1.6 | 1.8 | 1.8 | 1.8 |
| Hydrogen | 5.5 | 61.9 | 69.5 | 69.5 | 75.9 | 75.9 | 81.4 |
| Carbon Monoxide | 0.0 | 17.3 | 9.7 | 9.7 | 10.6 | 10.6 | 11.3 |
| Water | 59.4 | 16.2 | 8.7 | 8.7 | 0.3 | 0.3 | 0.0 |
| Methanol | 0.0 | 0.0 | 0.0 | 0.0 | 0.0 | 0.0 | 0.0 |

TABLE 2

| Stream ID | 51 | 62 | 72 | 71 | 61 | 82 |
|---|---|---|---|---|---|---|
| Temperature (° C.) | 250 | 40 | 40 | 40 | 40 | −70 |
| Pressure (bar g) | 86.2 | 85.2 | 0.5 | 84.7 | 85.2 | 87.7 |
| Total Flow ($Nm^3/h$) | 3047 | 2481 | 371 | 2109 | 566 | 287 |
| Composition [mole %] | | | | | | |
| Carbon Dioxide | 4.1 | 4.7 | 31.5 | 0.0 | 1.3 | 95.7 |
| Nitrogen | 0.5 | 0.6 | 3.8 | 0.1 | 0.0 | 0.0 |
| Methane | 2.4 | 3.0 | 19.7 | 0.0 | 0.1 | 1.2 |
| Hydrogen | 73.0 | 89.4 | 29.9 | 99.9 | 0.9 | 1.6 |
| Carbon Monoxide | 1.5 | 1.9 | 12.4 | 0.0 | 0.0 | 1.3 |
| Water | 2.5 | 0.0 | 0.1 | 0.0 | 13.5 | 0.1 |
| Methanol | 16.0 | 0.4 | 2.6 | 0.0 | 84.1 | 0.0 |

Example 2

Table 3 and 4 shows a similar embodiment of the invention as Example 1, but here the separation temperature in the cryogenic separation section is increased to −50° C., instead of −70° C. in Example 1. According to the method of the invention, this allows for producing a product split of 162 $Nm^3/h$ of $CO_2$ at a purity of 96% at 88 barg, 2036 $Nm^3/h$ of $H_2$ at a purity of 99.9% and 85 barg, and 627 $Nm^3/h$ CH 3 OH at a purity of 84% and 85 barg. Consequently the methanol to hydrogen ratio has decreased from 4.4 to 4.1.

TABLE 3

| Stream ID | 1 | 11 | 15 | 21 | 31 | 41 | 81 |
|---|---|---|---|---|---|---|---|
| Temperature (° C.) | 403 | 1015 | 438 | 40 | 40 | 219 | −60 |
| Pressure (bar g) | 26.4 | 25.0 | 23.5 | 22.5 | 22.5 | 88.3 | 87.7 |
| Total Flow ($Nm^3/h$) | 2929 | 4716 | 4716 | 4716 | 4318 | 4320 | 4145 |

TABLE 3-continued

| Stream ID | 1 | 11 | 15 | 21 | 31 | 41 | 81 |
|---|---|---|---|---|---|---|---|
| Composition [mole %] | | | | | | | |
| Carbon Dioxide | 1.4 | 2.6 | 10.1 | 10.1 | 11.0 | 11.0 | 7.8 |
| Nitrogen | 0.5 | 0.3 | 0.3 | 0.3 | 0.4 | 0.4 | 0.4 |
| Methane | 33.2 | 1.6 | 1.6 | 1.6 | 1.8 | 1.8 | 1.8 |
| Hydrogen | 5.5 | 61.9 | 69.5 | 69.5 | 75.9 | 75.9 | 79.0 |
| Carbon Monoxide | 0.0 | 17.3 | 9.7 | 9.7 | 10.6 | 10.6 | 11.0 |
| Water | 59.4 | 16.2 | 8.7 | 8.7 | 0.3 | 0.3 | 0.0 |
| Methanol | 0.0 | 0.0 | 0.0 | 0.0 | 0.0 | 0.0 | 0.0 |

TABLE 4

| Stream ID | 51 | 62 | 72 | 71 | 61 | 82 |
|---|---|---|---|---|---|---|
| Temperature (° C.) | 250 | 40 | 40 | 40 | 40 | −60 |
| Pressure (bar g) | 86.2 | 85.2 | 0.5 | 84.7 | 85.2 | 87.7 |
| Total Flow ($Nm^3/h$) | 3124 | 2498 | 462 | 2036 | 627 | 162 |
| Composition [mole %] | | | | | | |
| Carbon Dioxide | 6.8 | 8.0 | 43.5 | 0.0 | 2.0 | 95.5 |
| Nitrogen | 0.5 | 0.6 | 3.0 | 0.1 | 0.0 | 0.0 |
| Methane | 2.4 | 3.0 | 16.3 | 0.0 | 0.1 | 1.1 |
| Hydrogen | 68.7 | 85.7 | 23.2 | 99.9 | 0.8 | 1.9 |
| Carbon Monoxide | 1.8 | 2.2 | 11.8 | 0.0 | 0.0 | 1.3 |
| Water | 3.5 | 0.0 | 0.1 | 0.0 | 17.2 | 0.2 |
| Methanol | 16.3 | 0.4 | 2.0 | 0.0 | 79.9 | 0.0 |

The following numbered aspects are provided:

Aspect 1. A method for upgrading a hydrocarbon-containing feed gas to a methanol product stream and a hydrogen product stream, comprising the steps of:

a) providing a hydrocarbon-containing feed gas (1) to a reforming reactor (10), b) reforming said hydrocarbon-containing feed gas (1) in the reforming reactor (10), to provide a first synthesis gas stream (11), b1) optionally, feeding at least part of the first synthesis gas stream (11) from step b) to a water gas shift reactor (14) to provide shifted synthesis gas stream (15), c) cooling said first synthesis gas stream (11) and/or the shifted synthesis gas stream (15) in a cooling unit (20), to provide a second synthesis gas stream (21), d) removing water from said second synthesis gas stream (21), in a water removal unit (30), to provide a third synthesis gas stream (31), e) compressing said third synthesis gas stream (31) in a compressing unit (40) to a first pressure, said first pressure being higher than the feed pressure of said hydrocarbon feed gas, to provide a fourth synthesis gas stream (41), e1) optionally, feeding at least part of the fourth synthesis gas stream (41) from step e) to a $CO_2$ removal unit (80), to provide a $CO_2$-rich stream (82) and a fifth synthesis gas stream (81), f) feeding at least part of the fourth synthesis gas stream (41) and/or at least part of the fifth synthesis gas stream (81) from step (e) to a methanol synthesis unit (50), to provide a methanol-rich stream (51), g) feeding at least part of the methanol-rich stream (51) from step f) to a separation unit (60), to provide a methanol product stream (61) and a hydrogen rich stream (62).

Aspect 2. The method according to aspect 1, further comprising the step of adjusting the molar ratio between the hydrogen product stream and the methanol product stream.

Aspect 3. The method according to any of the preceding aspects, said method further comprising the step of adjusting the amount of $CO_2$ which is condensed in the $CO_2$ removal unit (80), relative to the $CO_2$ content in the fourth synthesis gas stream (41).

Aspect 4. The method according to aspect 3, wherein the $CO_2$ removal unit (80) is a cryogenic separation unit (80'), and wherein the increase in the amount of $CO_2$ condensed in the cryogenic separation unit (80') is achieved by decreasing the operating temperature in the cryogenic separation unit (80').

Aspect 5. The method according to any one of aspects 3-4, wherein a first part of the fourth synthesis gas stream (41) from step e) is fed to the $CO_2$ removal unit (80), to provide the $CO_2$-rich stream (82) and the fifth synthesis gas stream (81); and wherein at least part of the fifth synthesis gas stream (81) is fed to said methanol synthesis unit (50) together with a second part of the fourth synthesis gas stream (41) in step f.

Aspect 6. The method according to any of the preceding aspects, wherein said hydrocarbon-containing feed is a biogas.

Aspect 7. The method according to any of the preceding aspects, said method further comprising the step of providing a $CO_2$-containing feed (2) to said reforming reactor (10).

Aspect 8. The method according to aspect 7, said method further comprising the step of regulating the $CO_2$-containing feed (2) such that the module, defined as $$M = \frac{H_2 - CO_2}{CO + CO_2},$$

of said first synthesis gas stream is in the range of 1.5 to 2.5.

Aspect 9. The method according to any of the preceding aspects, wherein said reforming reactor (10) comprises an autothermal reformer, said method further comprising the step of providing an $O_2$-containing feed (3) to said autothermal reformer.

Aspect 10. The method according to aspect 9, said method further comprising the step of regulating the $O_2$-containing feed (3) such that the module, defined as $$M = \frac{H_2 - CO_2}{CO + CO_2},$$

of said first synthesis gas stream is in the range of 1.5 to 2.5.

Aspect 11. The method according to any of the preceding aspects, said method further comprising the step of providing an $H_2$-containing feed (4) upstream the methanol synthesis unit (50), preferably in admixture with the at least part of the fourth synthesis gas stream (41) and/or at least part of the fifth synthesis gas stream (81).

Aspect 12. The method according to aspect 11, said method further comprising the step of regulating the $H_2$-containing feed (4) such that the module, defined as $$M = \frac{H_2 - CO_2}{CO + CO_2},$$

of said fourth and/or fifth synthesis gas stream is in the range of 1.5 to 2.5.

Aspect 13. The method according to any of aspects 9-12, wherein an electrolysis unit is provided, and the method further comprises the step of generating an $H_2$-containing feed (4) and an $O_2$-containing feed (3) in said electrolysis unit from a water feedstock, said method further comprising the step(s) of supplying said $H_2$-containing feed (4) to the methanol synthesis unit (50) and/or supplying said $O_2$-containing feed (3) to the autothermal reformer.

Aspect 14. The method according to any one of aspects 7-13, wherein the molar ratio between the methanol product stream and the hydrogen product stream is changed by regulating the $CO_2$-containing feed (2), the $O_2$-containing feed (3), and/or the $H_2$-containing feed (4).

Aspect 15. The method according to any one of the preceding aspects, wherein said reforming reactor (10) comprises a tubular reformer, a convective reformer, an electrically heated reformer, an autothermal reformer, or a combination thereof, in particular, a combination of a tubular reformer placed in series with an autothermal reformer, or a combination of an electrically heated reformer placed in series with an autothermal reformer.

Aspect 16. The method according to aspect 15, wherein said reforming reactor (10) is an electrically heated reformer which preferably comprises a pressure shell housing a structured catalyst, wherein said structured catalyst comprises a macroscopic structure of an electrically conductive material, said macroscopic structure supporting a ceramic coating, where said ceramic coating supports a catalytically active material; and wherein the reforming step comprises the additional step of supplying electrical power via electrical conductors connecting an electrical power supply placed outside said pressure shell to said structured catalyst, allowing an electrical current to run through said macroscopic structure material, thereby heating at least part of the structured catalyst to a temperature of at least 500° C.

Aspect 17. The method according to aspect 16, wherein the electrical power supplied to the electrically heated reformer is generated by means of a renewable energy source.

Aspect 18. The method according to any one of the preceding aspects, wherein the separation unit (60) is a flash separation unit.

Aspect 19. The method according to any one of the preceding aspects, wherein a portion of the hydrogen rich stream (62) from step g) is compressed and returned to the methanol synthesis unit (50) as a methanol loop recycle stream.

Aspect 20. The method according to any one of the preceding aspects, further comprising the step of h) providing at least part of said hydrogen rich stream from step g) to a $H_2$ purification unit, to separate said hydrogen rich stream into a hydrogen product stream and an off-gas stream.

Aspect 21. The method according to aspect 20, wherein the $H_2$ purification unit (70) comprises a pressure-swing absorption (PSA) unit, a membrane unit or a cryogenic separation unit.

Aspect 22. A system for upgrading a hydrocarbon-containing feed gas to a methanol product stream and a hydrogen product stream, said system comprising:

a hydrocarbon-containing feed gas (1) arranged to be fed to a reforming reactor (10), reforming reactor (10) arranged to reform said hydrocarbon-containing feed gas (1); to thereby provide a first synthesis gas stream (11) from the reforming reactor (10), optionally, a water gas shift reactor (14) arranged to receive at least part of the first synthesis gas stream (11) from the reforming reactor and provide shifted synthesis gas stream (15), a cooling unit (20) arranged to cool said first synthesis gas stream (11) and/or the shifted synthesis gas stream (15) and thereby provide a second synthesis gas stream (21), a water removal unit (30) arranged to remove water from said second synthesis gas stream (21), and thereby provide a third synthesis gas stream (31), a compressing unit (40) arranged to compress said third synthesis gas stream (31) to a first pressure, said first pressure being higher than the feed pressure of said hydrocarbon feed gas, and thereby provide a fourth synthesis gas stream (41), optionally, a $CO_2$ removal unit (80), arranged to receive at least a part of the fourth synthesis gas stream (41) and to provide a $CO_2$-rich stream (82) and a fifth synthesis gas stream (81), a methanol synthesis unit (50) arranged to convert at least part of the fourth synthesis gas stream (41) and/or at least part of the fifth synthesis gas stream (81) to a methanol-rich stream (51), a separation unit (60), arranged to provide a methanol product stream (61) and a hydrogen rich stream (62) from at least part of the methanol-rich stream (51).

Aspect 23. The system according to aspect 22, wherein a first part of the fourth synthesis gas stream (41) is arranged to be fed to the $CO_2$ removal unit (80), to provide the $CO_2$-rich stream (82) and the fifth synthesis gas stream (81); and wherein at least part of the fifth synthesis gas stream (81) is arranged to be fed to said methanol synthesis unit (50) together with a second part of the fourth synthesis gas stream (41).

Aspect 24. The system according to any of aspects 22-23, said system further comprising a $CO_2$-containing feed (2) arranged to be fed to said reforming reactor (10), preferably in admixture with said hydrocarbon-containing feed gas (1).

Aspect 25. The system according to any of aspects 22-24, wherein said reforming reactor (10) comprises an autothermal reformer, said system further comprising an $O_2$-containing feed (3) arranged to be fed to said autothermal reformer.

Aspect 26. The system according to any of aspects 22-25, said system further comprising an $H_2$-containing feed (4) arranged to be fed upstream the methanol synthesis unit (50), preferably in admixture with the at least part of the fourth synthesis gas stream (41) and/or at least part of the fifth synthesis gas stream (81).

Aspect 27. The system according to any of aspects 22-26, said system further comprising an electrolysis unit, said electrolysis unit being arranged to generate an $H_2$-containing feed (4) and an $O_2$-containing feed (3) from a water feedstock, said system being further arranged to supply said $H_2$-containing feed (4) from said electrolysis unit to the methanol synthesis unit (50) and/or supply said $O_2$ containing feed (3) from said electrolysis unit to the autothermal reformer.

Aspect 28. The system according to any of aspects 22-27, wherein said reforming reactor (10) comprises a tubular reformer, a convective reformer, an electrically heated reformer, an autothermal reformer, or a combination thereof, in particular, a combination of a tubular reformer placed in series with an autothermal reformer, or a combination of an electrically heated reformer placed in series with an autothermal reformer.

Aspect 29. The system according to aspect 28, wherein said reforming reactor (10) is an electrically heated reformer which preferably comprises a pressure shell housing a structured catalyst, wherein said structured catalyst comprises a macroscopic structure of an electrically conductive material, said macroscopic structure supporting a ceramic coating, where said ceramic coating supports a catalytically active material; and wherein electrical conductors connecting an electrical power supply are placed outside said pressure shell and arranged to supply electrical power to said structured catalyst, thereby allowing an electrical current to run through said macroscopic structure material, and thereby heating at least part of the structured catalyst to a temperature of at least 500° C.

Aspect 30. The system according to any one of aspects 22-29, wherein the separation unit (60) is a flash separation unit.

Aspect 31. The system according to any of aspects 22-30, said system further comprising a $H_2$ purification unit (70), arranged to separate said hydrogen-rich stream (62) into a hydrogen product stream (71) and an off-gas stream (72)

Aspect 32. The system according to aspect 31, wherein the $H_2$ purification unit (70) is a pressure-swing absorption (PSA) unit, a membrane unit or a cryogenic separation unit.

Aspect 33. The system according to any one of aspects 22-32, wherein the $CO_2$ removal unit (80) is a cryogenic separation unit (80').

The invention claimed is:

1. A method for upgrading a hydrocarbon-containing feed gas to a methanol product stream and a hydrogen product stream, comprising the steps of:

a) providing a hydrocarbon-containing feed gas to a reforming reactor, b) reforming said hydrocarbon-containing feed gas in the reforming reactor, to provide a first synthesis gas stream, b1) optionally, feeding at least part of the first synthesis gas stream from step b) to a water gas shift reactor to provide shifted synthesis gas stream, c) cooling said first synthesis gas stream and/or the shifted synthesis gas stream in a cooling unit, to provide a second synthesis gas stream, d) removing water from said second synthesis gas stream, in a water removal unit, to provide a third synthesis gas stream, e) compressing said third synthesis gas stream in a compressing unit to a first pressure, said first pressure being higher than the feed pressure of said hydrocarbon feed gas, to provide a fourth synthesis gas stream, e1) feeding at least part of the fourth synthesis gas stream from step e) to a $CO_2$ removal unit, to provide a $CO_2$-rich stream and a fifth synthesis gas stream, f) feeding at least part of the fourth synthesis gas stream and at least part of the fifth synthesis gas stream from steps (e) and (e1) to a methanol synthesis unit, or feeding at least part of the fifth synthesis gas stream from step (e1) to the methanol synthesis unit, to provide a methanol-rich stream, g) feeding at least part of the methanol-rich stream from step f) to a separation unit, to provide a methanol product stream and a hydrogen rich stream, wherein the methanol synthesis unit is free of input from the $CO_2$-rich stream.

2. The method according to claim 1, further comprising the step of adjusting the molar ratio between the hydrogen product stream and the methanol product stream.

3. The method according to claim 1, said method further comprising the step of adjusting the amount of $CO_2$ which is removed in the $CO_2$ removal unit, relative to the $CO_2$ content in the fourth synthesis gas stream.

4. The method according to claim 3, wherein the $CO_2$ removal unit is a cryogenic separation unit, and wherein the increase in the amount of $CO_2$ removed in the cryogenic separation unit is achieved by decreasing the operating temperature in the cryogenic separation unit.

5. The method according to claim 3, wherein a first part of the fourth synthesis gas stream from step e) is fed to the $CO_2$ removal unit, to provide the $CO_2$-rich stream and the fifth synthesis gas stream; and wherein at least part of the fifth synthesis gas stream is fed to said methanol synthesis unit together with a second part of the fourth synthesis gas stream in step f).

6. The method according to claim 1, said method further comprising the step of providing a $CO_2$-containing feed to said reforming reactor.

7. The method according to claim 1, wherein said reforming reactor comprises an autothermal reformer, said method further comprising the step of providing an $O_2$-containing feed to said autothermal reformer.

8. The method according to claim 1, said method further comprising the step of providing an $H_2$-containing feed upstream the methanol synthesis unit.

9. The method according to claim 6, wherein the molar ratio between the methanol product stream and the hydrogen product stream is changed by regulating the $CO_2$-containing feed, an $O_2$-containing feed, and/or an $H_2$-containing feed.

10. The method according to claim 1, wherein said reforming reactor comprises a tubular reformer, a convective reformer, an electrically heated reformer, an autothermal reformer, or a combination thereof.

11. The method according to claim 1, wherein a portion of the hydrogen rich stream from step g) is compressed and returned to the methanol synthesis unit as a methanol loop recycle stream.

12. The method according to claim 1, wherein the method is configured to selectively operate in:

(i) a first mode producing increased $CO_2$ and hydrogen with reduced methanol production; and (ii) a second mode producing increased methanol with reduced $CO_2$ and hydrogen production.

13. The method according to claim 1, further comprising the step of:

h) using a $H_2$ purification unit, separating said hydrogen-rich stream into the hydrogen product stream and an off-gas stream.

14. The method according to claim 13, comprising operating the $CO_2$ removal unit and the methanol synthesis unit at elevated and similar pressures, wherein a first part of the fourth synthesis gas stream from step e) is fed to the $CO_2$ removal unit, to provide the $CO_2$-rich stream and the fifth synthesis gas stream, and wherein at least part of the fifth synthesis gas stream is fed to said methanol synthesis unit together with a second part of the fourth synthesis gas stream in step f.

15. A method for upgrading a hydrocarbon-containing feed gas to a methanol product stream and a hydrogen product stream, comprising the steps of:

a) providing a hydrocarbon-containing feed gas to a reforming reactor, b) reforming said hydrocarbon-containing feed gas in the reforming reactor, to provide a first synthesis gas stream, b1) optionally, feeding at least part of the first synthesis gas stream from step b) to a water gas shift reactor to provide shifted synthesis gas stream, c) cooling said first synthesis gas stream and/or the shifted synthesis gas stream in a cooling unit, to provide a second synthesis gas stream, d) removing water from said second synthesis gas stream, in a water removal unit, to provide a third synthesis gas stream, e) compressing said third synthesis gas stream in a compressing unit to a first pressure, said first pressure being higher than the feed pressure of said hydrocarbon feed gas, to provide a fourth synthesis gas stream, e1) feeding at least part of the fourth synthesis gas stream from step e) to a $CO_2$ removal unit, to provide a $CO_2$-rich stream and a fifth synthesis gas stream, f) feeding at least part of the fourth synthesis gas stream and at least part of the fifth synthesis gas stream, directly from the $CO_2$ removal unit, from steps (e) and (e1) to a methanol synthesis unit, or feeding at least part of the fifth synthesis gas stream, directly from the $CO_2$ removal unit, from step (e1) to the methanol synthesis unit, to provide a methanol-rich stream, g) feeding at least part of the methanol-rich stream from step f) to a separation unit, to provide a methanol product stream and a hydrogen rich stream.

* * * * *